United States Patent [19]

Davis et al.

[11] 4,010,190
[45] Mar. 1, 1977

[54] PRECURSORS FOR INSECTICIDES
[75] Inventors: Royston H. Davis; Derek A. Wood; Herbert P. Rosinger, all of Sittingbourne; Ronald F. Mason, Ashford, all of England
[73] Assignee: Shell Oil Company, Houston, Tex.
[22] Filed: Apr. 30, 1976
[21] Appl. No.: 681,939
[30] Foreign Application Priority Data
May 2, 1975 United Kingdom ............. 18438/75
[52] U.S. Cl. ........................................... 260/465 D
[51] Int. Cl.² ...................................... C07C 121/66
[58] Field of Search ............................... 260/465 D

[56] References Cited
UNITED STATES PATENTS
3,865,821  2/1975  Cordier et al. ............ 260/465 D X Primary Examiner—Dolph H. Torrence

[57] ABSTRACT

Alkyl esters of 3-cyano-3-(3-phenoxyphenyl)-2-ketopropionic acid, useful as precursors for the preparation of insecticidal esters of 3-phenoxy-α-cyanobenzyl alcohol.

2 Claims, No Drawings

PRECURSORS FOR INSECTICIDES

BACKGROUND OF THE INVENTION

U.S. Pat. No. 3,835,176 discloses insecticidal esters of 3-phenoxy-α-cyanobenzyl alcohol, and teaches that such esters can be prepared from 3-phenoxy-α-cyanobenzyl halides, such as the chloride or bromide. Applicant has found that the bromide can be prepared readily and efficiently by treating an alkyl ester of 3-cyano-3-(3-phenoxybenzyl)-2-ketopropionic acid with a brominating agent.

DESCRIPTION OF THE INVENTION

The alkyl esters provided by this invention have the formula

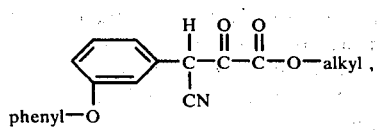

thus being alkyl esters of 3-cyano-3-(3-phenoxyphenyl)-2-ketopropionic acid. The alkyl moiety suitably contains from one to six carbon atoms and can be either straight-chain or branched-chain in configuration.

These esters are readily prepared by treating 3-phenoxybenzyl cyanide with a mono- or di-($C_{1-6}$)alkyl ester of oxalic acid in the presence of a strong base, then neutralizing the resulting reaction mixture.

The oxalate esters are a known class of compounds. Preparation of 3-phenoxybenzyl cyanide is described in Example 2, following.

Treatment of the benzyl cyanide with the oxalate ester can be suitably carried out using stoichiometric amounts of the reactants. It has been found that a slight excess of the ester, e.g., 2 to 10 mole percent excess, may be desirable to ensure complete reaction.

The treatment is carried out in the presence of a strong base. Suitable bases comprise alkali- and alkaline earth metal hydroxides such as sodium- or potassium hydroxide, alkali metal alkoxides such as sodium- or potassium methoxide or ethoxide as well as tetraalkylammonium hydroxide. Normally, 0.01 to 5 percent by weight of base calculated on the basis of the amount of benzyl cyanide, will be satisfactory. Use of a higher amount of base is not excluded, however.

The treatment can be carried out in the presence of a solvent such as methanol, ethanol, benzene or toluene. In case sodium ethoxide is used as the base, preference is given to ethanol as the solvent whereas benzene is preferred as the solvent when sodium methoxide is used as the base. The amount of solvent used is not critical. It should be noted that when a mono-ester of oxalic acid is used, the presence of an alcohol would lead to a simultaneously occuring esterification reaction leading to formation of the appropriate di-ester of oxalic acid, which will also be used as a starting material.

The treatment is suitably carried out at a slightly elevated temperature, e.g., from 30° C up to the boiling point of the solvent used. Good results have been obtained using temperatures in the range of from 40° C to 60° C. Although the reaction is normally carried out at autogeneous pressure, pressures up to 10 atmospheres can be readily used.

To ensure a maximum yield of the desired product, the base, preferably dissolved in solvent, should be added gradually with stirring to a mixture of the reactants, preferably dissolved in solvent. After the addition of the base has been completed, the reaction mixture may be stirred while allowing it to cool down to ambient temperature.

The working up procedures to be used in the process according to the present invention are known in the art and comprise acidifying the alkaline reaction mixture, preferably — particularly in large scale operations — by pouring it into a cold aqueous solution of hydrochloric acid or sulphuric acid. The product can be obtained from the semi-solid precipitate by extracting the precipitate one or more times with methylene dichloride or chloroform, followed by one or more water washings. If necessary, further washings using apolar solvents such as toluene or hexane or mixtures of such solvents can be used as well.

The ester product thus obtained is a racemic mixture, from which the individual components can be isolated, if necessary, by methods and techniques known in the art.

The ester can be converted to the α-cyanobenzyl bromide by treating the ester with a bromine source, such as bromine (in chloroform), N-bromosuccinimide or mixtures of bromine and chlorine, in the presence of a mild base, such as sodium acetate, to avoid side reactions that might result from the presence of the acid bromide byproduct.

Preparation of a typical (ethyl) ester of the invention in particular instances is shown in the following examples.

EXAMPLE 1

284 g of 3-phenoxy benzyl cyanide and 220 g of di-ethyl oxalate were mixed and 400 ml of absolute ethanol was added. To this mixture was added gradually a solution of sodium ethoxide (prepared by dissolving 31 g of sodium in 410 ml of absolute ethanol). After the addition of the ethanol solution the mixture was warmed to 50° C for 30 minutes and then allowed to stand at room temperature for 12 hours.

The reaction mixture was then acidified with ice-cooled 10% sulphuric acid (prepared by adding 37 ml of concentrated sulphuric acid to sufficient ice to give 370 ml of ice-cooled diluted acid). The product was extracted with methylene dichloride and the methylene dichloride solution was then washed neutral with distilled water. The product was dried over anhydrous sodium sulphate and the solvent removed. This product was treated with cold hexane to give ethyl 3-cyano-3-(3-phenoxyphenyl)-2-ketopropionate, melting point: 105°–109°, 90%. The structure was confirmed with proton magnetic resonance analysis (purity > 95%).

The preparation of the cyanide from the bromide is illustrated in the following example.

EXAMPLE 2

41 kg of 3-phenoxybenzyl bromide (Belgian Pat. No. 809,967; copending application Ser. No. 665,991, filed Mar. 11, 1976 was added over a 3.25 hour period to a cooled (10°) stirred mixture of 10.1 kg of sodium cyanide, 1.5 kg of sodium iodide and 50 liters of methanol. After the initial exothermic reaction, the mixture was allowed to warm to room temperature and was stirred overnight. 50 liters of water and 80 liters of toluene were then added and the aqueous phase was discarded.

Evaporation of the solvent gave a dark-brown oil, which was dissolved in 20 liters of ethanol and treated with 27 kg of diethyl oxalate. A solution of sodium ethoxide (prepared from 4.14 kg of sodium and ethanol (70 liters)) was then added during 45 minutes while the reaction temperature rose to 44° C. The mixture was stirred overnight and then poured into an ice-cold solution of hydrochloric acid (15 liters concentrated hydrochloric acid in 120 liters water). During acidification the temperature was kept at 0° C. The semi-solid product was extracted with chloroform (50 liters) and the organic phase was separated, washed with water (50 liters) and then evaporated to low bulk. The resulting oily slurry was diluted with petroleum spirit (30 liters) and the product filtered off, washed with a 20% solution of chloroform in petrol (20 liters), and then air-dried to give the ester, as a pale cream crystalline solid, m.p.: 110.5°–114° C.

Conversion of the ester to the bromonitrile is illustrated in the following examples.

EXAMPLE 3

The ethyl ester prepared in Example 2 was stirred with 31.3 kg of sodium acetate trihydrate in 100 liters of chloroform, and the mixture was cooled to 0° C. A solution of 19.8 kg of bromine in 25 liters of chloroform was then added over a 5-hour period to the stirred mixture at 0°–5° C. The mixture was allowed to stand overnight at room temperature.

The mixture was washed with water (50 liters) and the organic phase was then washed with saturated sodium bicarbonate solution (60 liters) until neutral. The chloroform solution was finally washed with water (50 liters) before evaporating almost to dryness (50° C/100 Torr.). The resulting oil was diluted with 30 liters of petroleum spirit and the mixture was then stirred overnight at room temperature. The crystalline product was filtered off and then washed with petroleum spirit containing 5% chloroform (25 liters) to give the bromonitrile as a pale-cream solid, m.p.: 68°–70° C.

EXAMPLE 4

A 10 liter flask was charged with 2.2 kg of the ethyl ester, 5 liters of methylene dichloride and 1.8 kg of sodium acetate trihydrate. This mixture was stirred and cooled to 5° C in an ice-bath, followed by the addition of 1.15 kg of bromine in 2.5 liters of methylene dichloride over a period of 1 hour. The temperature was kept below 5° C and stirring was continued for a further 2 hours.

After washing the reaction mixture with iced water and an ice cold saturated sodium bicarbonate solution, the solvent was removed and the crude product crystallized from cyclohexane/benzene 4/1 at 0°–5° C, to give the bromonitrile, m.p.: 66° C–67° C.

We claim:
1. A compound of the formula

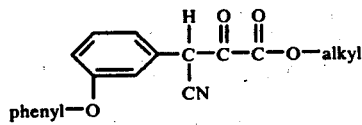

wherein the alkyl moiety contains from one to six carbon atoms.

2. A compound according to claim 1 wherein the alkyl moiety is ethyl.

* * * * *